United States Patent
Slanda et al.

[11] Patent Number: 6,053,899
[45] Date of Patent: Apr. 25, 2000

[54] MATERIAL DELIVERY DEVICE AND METHOD OF USING THE SAME

[75] Inventors: Josef Slanda, Milford; David Sauvageau, Metuhen; Barry N. Gellman, N. Easton; Armand Morin, Berkley, all of Mass.

[73] Assignee: Scimed Life Systems, Inc., Maple Grove, Minn.

[21] Appl. No.: 09/163,692

[22] Filed: Sep. 30, 1998

Related U.S. Application Data

[60] Provisional application No. 60/060,842, Oct. 2, 1997.

[51] Int. Cl.[7] .................................................. A61M 25/00
[52] U.S. Cl. ........................ 604/500; 604/506; 604/508; 604/523; 604/60; 604/84
[58] Field of Search ............................... 604/523, 59, 60, 604/500, 502, 506, 507, 508, 84

[56] References Cited

U.S. PATENT DOCUMENTS

| | | |
|---|---|---|
| 4,197,846 | 4/1980 | Bucalo . |
| 5,243,997 | 9/1993 | Uflacker et al. . |
| 5,342,394 | 8/1994 | Matsuno et al. . |
| 5,443,078 | 8/1995 | Uflacker . |
| 5,524,635 | 6/1996 | Uflacker et al. . |
| 5,632,746 | 5/1997 | Middleman et al. . |
| 5,713,948 | 2/1998 | Uflacker . |

FOREIGN PATENT DOCUMENTS

| | | |
|---|---|---|
| 563983 A1 | 10/1993 | European Pat. Off. . |
| WO 9604954 A1 | 2/1996 | WIPO . |
| WO 97/19643 | 6/1997 | WIPO . |

OTHER PUBLICATIONS

Translation of WO 96/04954, "Implant, Implatation–Method, and Application–Device".

*Primary Examiner*—John D. Yasko
*Attorney, Agent, or Firm*—Testa, Hurwitz & Thibeault, LLP

[57] ABSTRACT

A device, and related method, for introducing fiber material into a body includes a tubular member with a lumen extending to an opening in a distal end portion of the tubular member and a mechanism in the tubular member for passing the fiber material through the lumen and the opening and into the body. The mechanism can be a helical member rotatable within the tubular member to convey the fiber material through at least a portion of the lumen, out of the opening, and into the body, and the fiber material can be particles in a carrier that are injected into the lumen by a syringe coupled to the tubular member. The mechanism alternatively can be a sleeve slidable within the tubular member to force the fiber material through at least a portion of the lumen, out of the opening, and into the body, and the fiber material can be a suture or thread that is fed into a distal portion of the tubular member where it collects until it is forced out of the opening by the sleeve. The mechanism also can be a push rod slidable within the tubular member to push the fiber material through at least a portion of the lumen, out of the opening, and into the body, and the fiber material can be one or more pellets.

16 Claims, 13 Drawing Sheets

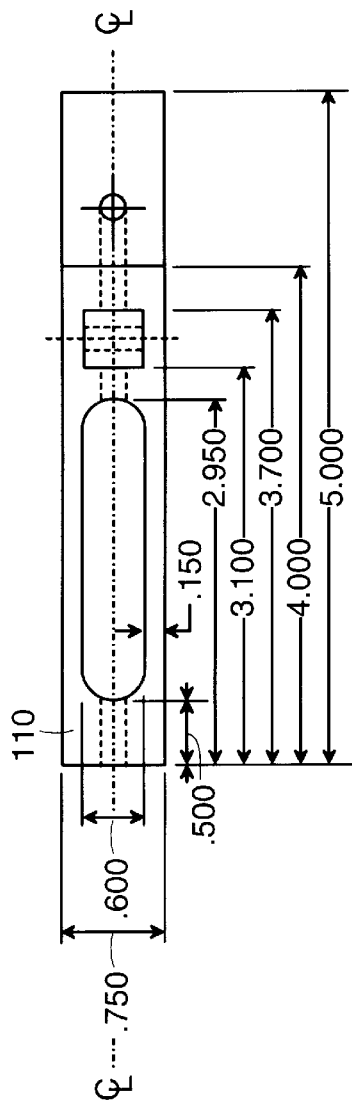
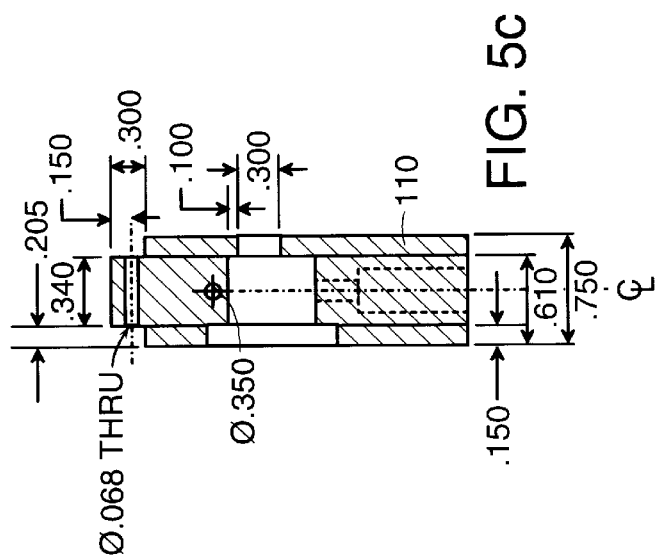
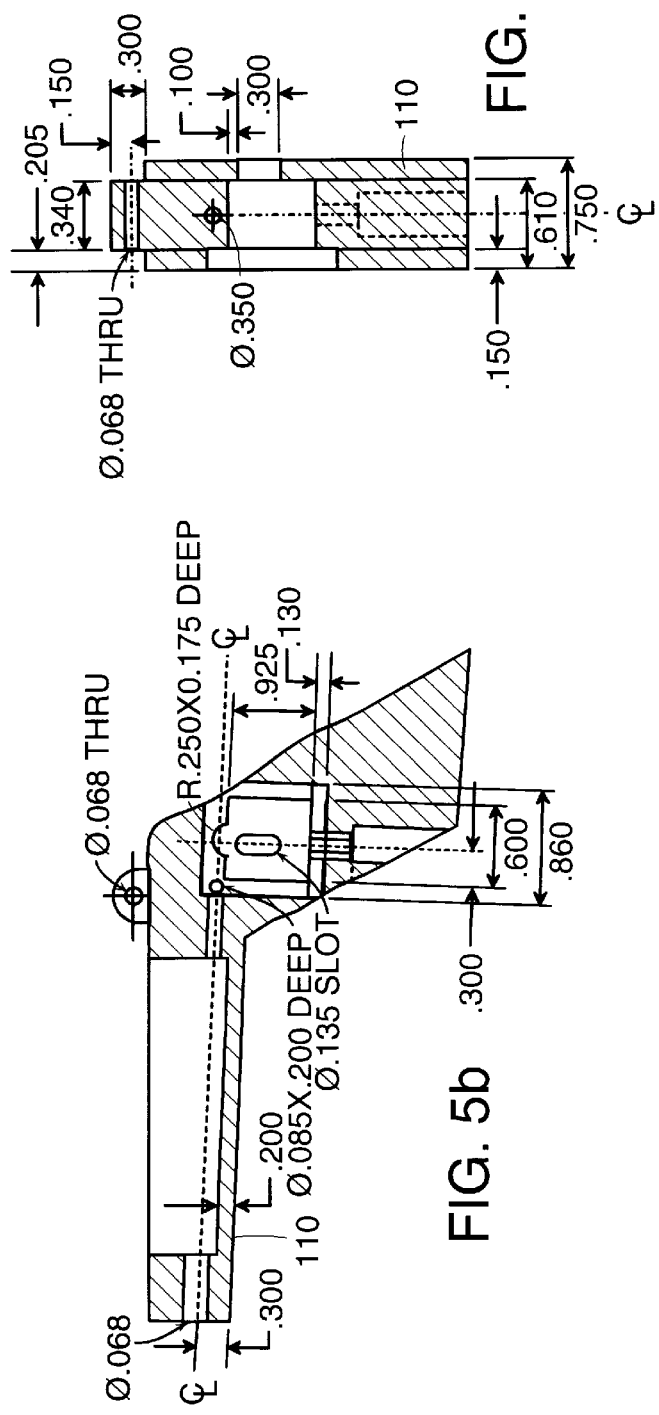
FIG. 5a
FIG. 5b
FIG. 5c

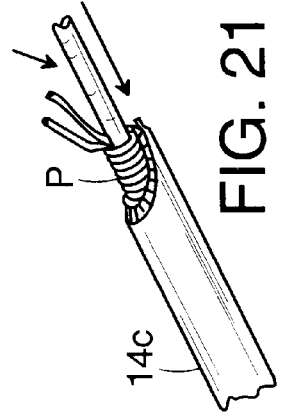
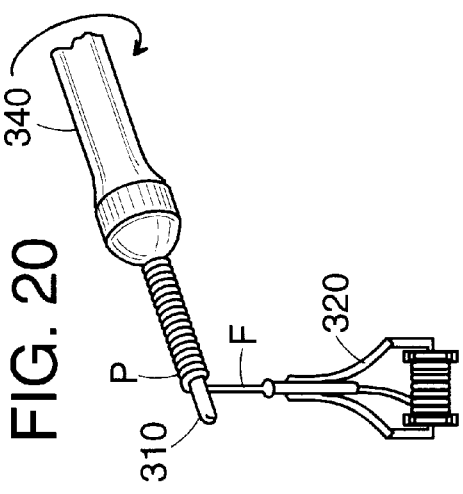
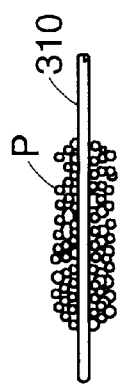
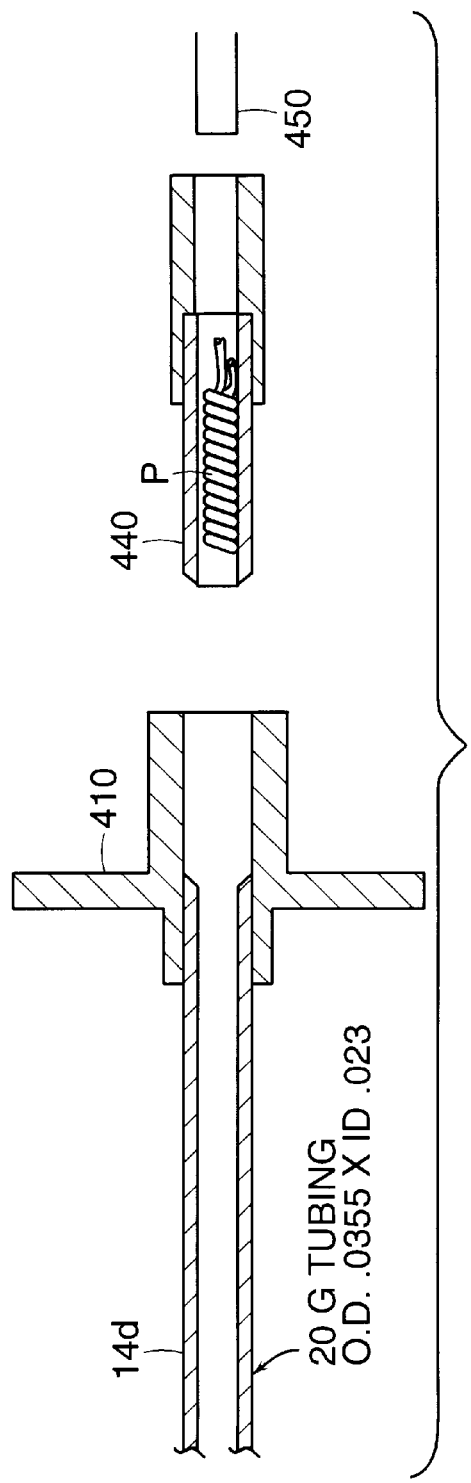

MATERIAL DELIVERY DEVICE AND METHOD OF USING THE SAME

CROSS-REFERENCE TO RELATED APPLICATION

This incorporates by reference and claims priority to and the benefit of U.S. provisional patent application serial No. 60/060,842 which was filed on Oct. 2, 1997.

TECHNICAL FIELD

This invention relates to a device for delivering material into the body and a method of using such a device. More particularly, the present invention relates to feeding a fiber or particles through a tubular member, such as a needle.

BACKGROUND INFORMATION

Many different types of medical and surgical treatments require a mass of material to be implanted in the body. For example, in one type of procedure for treating urinary incontinence, material is delivered to radial sites about the urethra to bulk tissue around the urethra. In other procedures, materials, such as bulking materials, are implanted in the body to treat aneurysms and arteriovenous malformations (AVMs), for example.

One type of bulking material currently approved by the FDA is a mixture of a phosphate carrier and either collagen or fat. However, this type of material is absorbed in the body within about one year and sometimes needs to be reinjected into a patient periodically. Other materials, such as TEFLON and silicone, have been tested, but some of these materials may be capable of migrating to vital organs of the body, such as the brain or the lungs, and thereby harm a patient.

SUMMARY OF THE INVENTION

The invention relates to the use of fiber materials, such as threads and sutures, in bulking tissue. These fiber materials provide a permanent bulking, and are not absorbed in or by the body. The fiber materials can be made of the same substances used to form surgical sutures and wound care products that have a long, successful, and safe history when used for patient implantation.

It is an object of the invention to provide devices and methods for delivering fiber materials into the body for a variety of different uses.

It is another object to provide devices and methods for dispensing fiber material (e.g., a fiber thread or a fiber pellet) into a body to bulk tissue to, for example, treat urinary incontinence.

In treating urinary incontinence, devices and methods according to the invention are used to deliver the fiber material to radial sites about the urethra, and the fiber material provides bulking of tissue around the urethra to enable the patient to be continent permanently. That is, placing the fiber material at radial sites about the urethra forces coaptation of this valve and thus enables the patient to be continent permanently.

It is a further object to provide devices and methods for directing the fiber material into a patient's body with sufficient force to maintain long-term bulking of tissue with the fiber material.

In one aspect, the invention involves a device for introducing fiber material into a body. The device comprises a tubular member having a lumen extending to an opening in a distal end portion of the tubular member. The device also comprises a mechanism in the tubular member for passing the fiber material through the lumen and the opening and into the body.

In another aspect, the invention relates to a device for introducing fiber material into a body. The device comprises a tubular member having a lumen extending to an opening in a distal end portion of the tubular member, and a helical member within the tubular member for conveying the fiber material through at least a portion of the lumen, out of the opening, and into the body. A syringe can be coupled to the tubular member in communication with the lumen, and the syringe can provide the fiber material into the lumen of the tubular member. The fiber material can comprise particles in a carrier such as a gel or liquid carrier.

In yet another aspect, the invention features a device for introducing fiber material into a body. The device comprises a tubular member having a lumen extending to an opening in a distal end portion of the tubular member, and a sleeve slidable within the tubular member for forcing the fiber material through at least a portion of the lumen, out of the opening, and into the body. A driving roller can feed the fiber material into a distal portion of the tubular member until the fiber material accumulates inside the distal portion, and then the sleeve can be moved to force the accumulated fiber material out of the opening in the distal end portion of the tubular member and into the body. The fiber material can comprise a suture or a thread.

In still another aspect, the invention involves a device for introducing fiber material into a body. The device comprises a tubular member having a lumen extending to an opening in a distal end portion of the tubular member, and a push rod slidable within the tubular member for pushing the fiber material through at least a portion of the lumen, out of the opening, and into the body. The fiber material can comprise one or more pellets.

In yet still another aspect, the invention relates to a method of introducing fiber material into a body. The method comprises providing a device including (i) a tubular member having a lumen extending to an opening in a distal end portion of the tubular member and (ii) a mechanism in the tubular member for passing the fiber material through the lumen and the opening and into the body. The method further comprises introducing the tubular member of the device into the body, and operating the mechanism in the tubular member of the device to pass the fiber material through the opening in the distal end portion of the tubular member and into the body.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 5a is a top view of a housing of the device of FIG. 2.

FIG. 5b is a cross sectional view of the housing of FIG. 5a.

FIG. 5c is a cross sectional view of the housing of FIG. 5a.

FIG. 6b is a side view of the pivot arm of FIG. 6a.

FIG. 7b is a side view of the coupler of FIG. 7a.

FIG. 7c is a top view of the coupler of FIG. 7a.

FIG. 8b is a front view of the roller mount of FIG. 8a.

FIG. 8c is a top view of the roller mount of FIG. 8a.

FIG. 9b is a side view of the advancing lever of FIG. 9a.

FIG. 10b is a front view of the drive roller of FIG. 10a.

FIG. 11b is a side view of the driving knob of FIG. 11a.

FIG. 12b is a side view of the drive mechanism cover of FIG. 12a.

FIGS. 13b and 13c are cross sectional views of the device of FIG. 13a.

FIG. 14a is a top view of a housing shown in FIG. 13a.

FIGS. 14b and 14c are cross sectional views of the housing of FIG. 14a.

FIG. 14d is a rear view of the housing of FIG. 14a.

FIG. 15a is a bottom view of an advancing lever shown in FIG. 13a.

FIG. 15b is a side view of the advancing lever of FIG. 13a.

FIG. 16a is a rear view of a pivot arm shown in FIG. 13a.

FIG. 16b is a side view of the pivot arm of FIG. 16a.

FIG. 17a is a front view of a coupler shown in FIG. 13a.

FIG. 17b is a side view of the coupler of FIG. 17a.

FIG. 17c is a top view of the coupler of FIG. 17a.

FIG. 18 shows three layers of fiber wound on a mandrel to form a fiber pellet for loading in one of the devices.

FIG. 19 shows two layers of fiber wound on a mandrel to form a fiber pellet for loading in one of the devices.

FIG. 20 shows structure for winding the fiber on the mandrel to form a pellet.

FIG. 21 shows a way in which a fiber pellet is loaded in one of the devices.

FIG. 22 shows a way in which the fiber pellet is loaded in the devices.

DESCRIPTION

The present invention is directed to a device for delivering a fiber through a tubular member, such as a hypodermic needle. As used herein, the term fiber or fiber material includes one or more fiber strands, suture material, or thread material, for example. The fiber is preferably made of material comprising polypropylene, nylon, polyester, silk, and/or cross linked polysaccharide, such as calcium alginate. For example, the fiber is preferably polypropylene suture, polyester suture, calcium alginate thread, or silk suture. In addition, the fiber alternatively includes polyester, polypropylene, silk and/or calcium alginate fibrous material having a length or diameter of about 100 microns to about 200 microns.

Preferably, the device is capable of delivering the fiber material to radial sites about the urethra. The fiber material provides bulking of tissue around the urethra, thus enabling the patient to be permanently continent.

Preferably, the device does not use a carrier, such as saline solution or phosphate solution, to carry the fiber and to open the tissue planes. The device is preferably capable of directing the fiber into the body with a sufficient force to maintain long-term bulking of tissue.

Figure 1:
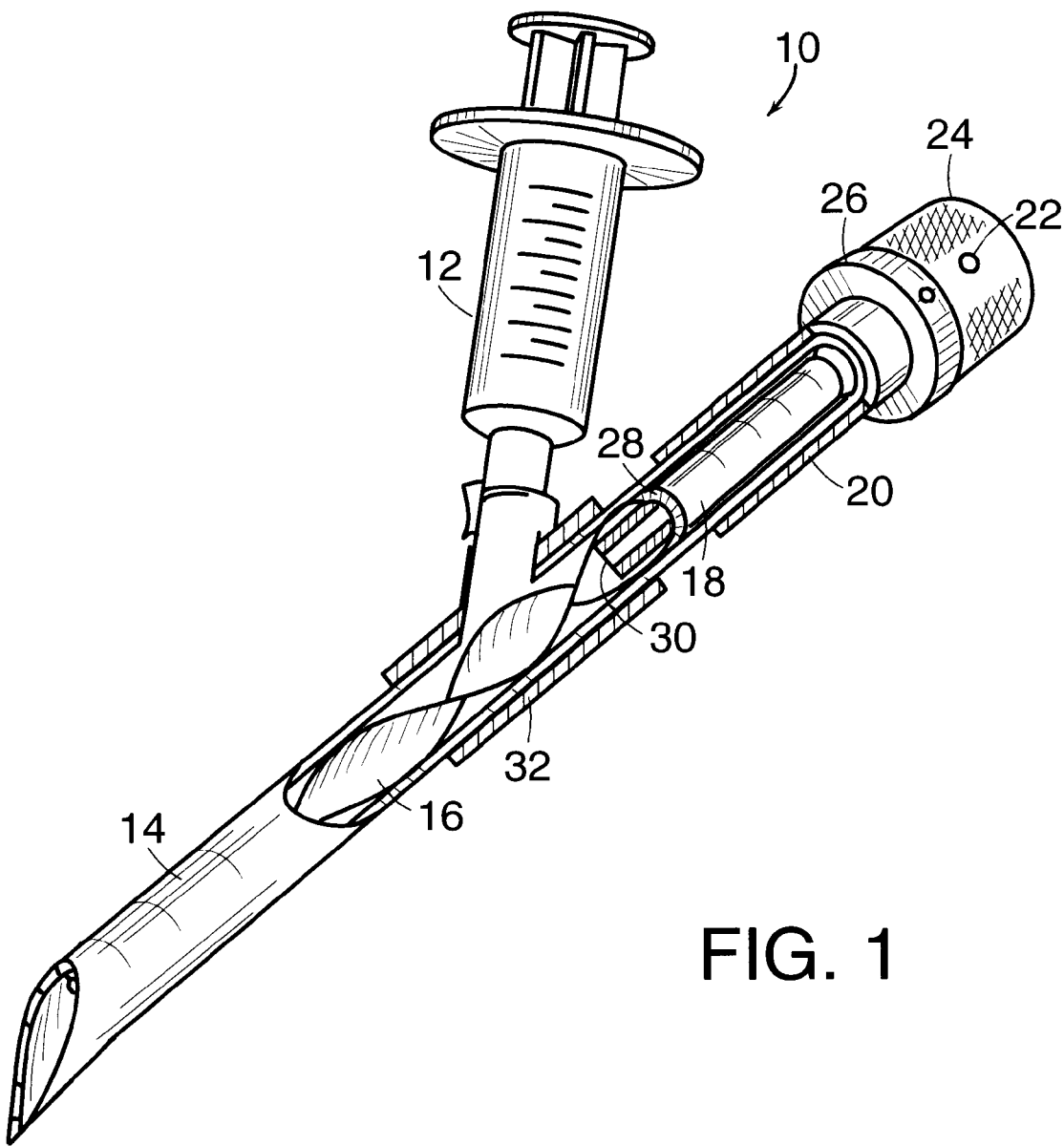
FIG. 1 is a perspective view of a first embodiment of a material delivery device in accordance with the invention with portions of the device removed to reveal internal components of the device.

FIG. 1 shows a first embodiment of a device 10 for delivering the fiber. The device 10 includes a syringe 12 coupled to a tubular member 14 via a Y-shaped luer adapter 32. The syringe 12 includes a slidable plunger and a barrel filled with the fiber. Alternatively, the barrel of the syringe 12 contains other materials or particles for delivery into the body and for bulking of tissue. When the plunger of the syringe 12 is pressed, the material in the barrel of the syringe 12 passes into the tubular member 14. The tubular member 14 is preferably a needle or tube having a gauge of about 16 and a length of about 10 inches. Optionally, the tubular member 14 is joined to the adapter 32 with an adhesive.

As shown in FIG. 1, a helical member 16 is provided in a lumen of the tubular member 14. The helical member 16 is shaped like an impeller, corkscrew, or auger. Rotation of a driving knob 24 rotates the helical member 16 in the lumen of the tubular member 14 so that the helical member 16 conveys bulking material (fiber) along the length of the tubular member 14 and through an opening in a distal portion of the tubular member 14.

A brazed connection 30 joins the helical member 16 to a mandrel 18, and the mandrel 18 is connected to the driving knob 24 via a set screw 22. A tubular housing 20 for the mandrel 18 has a distal end connected to a leg of the adapter 32. A driving lock 26 threaded on a proximal portion of the tubular housing 20 is rotatable to prevent (or provide resistance to) rotation of the driving knob 24. An o-ring seal 28 maintains a seal between the tubular housing 20 and the rotatable mandrel 18.

To use the device 10, the tubular member 14 is inserted in the body. The plunger of the syringe 12 is pressed to pass material from the syringe 12 to the tubular member 14. The driving knob 24 is rotated to rotate the helical member 16 and thereby convey the material through both the tubular member 14 and the opening in the tubular member 14.

The barrel of the syringe 12 may be filled with many different types of materials, such as suture material, flat textured yarn material, ground suture material, or ground fabric polyester material. Preferably, the syringe 12 contains a paste or compound like substance, such as particles in a gel or liquid carrier. In the alternative, the syringe 12 contains a mixture of chopped suture and compound.

FIGS. 2–4, 5a, 5b, 5c, 6a, 6b, 7a, 7b, 7c, 8a, 8b, 8c, 9a, 9b, 10a, 10b, 11a, 11b, 12a, and 12b show a second embodiment of a device 100 for delivering fiber in the body. As shown in FIGS. 2–4, 5a, 5b, and 5c, the device 100 includes a housing 110 and a tubular member 14a coupled to the housing 110 at a proximal end of the tubular member 14a. Preferably, the tubular member 14a is a needle or tube connected directly to the housing 110. Alternatively, the tubular member 14a is releasably coupled to the housing 110 via an adapter (not shown).

Figure 3:
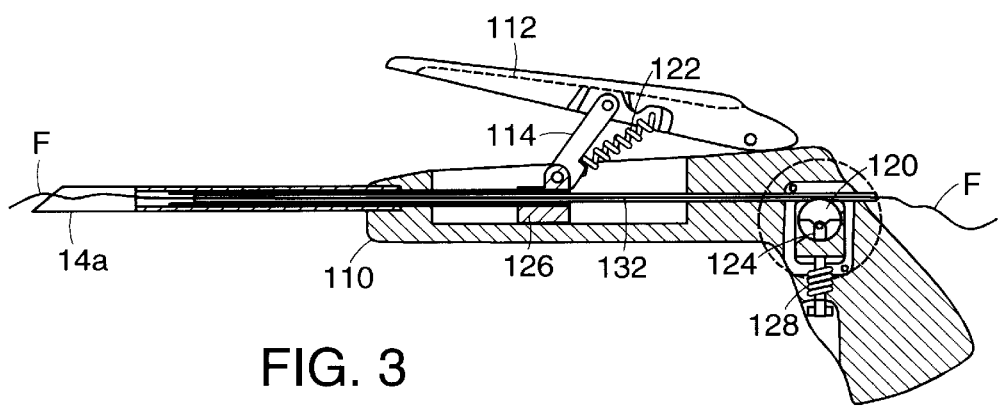
FIG. 3 is a cross sectional view of the device of FIG. 2.
Figure 4:
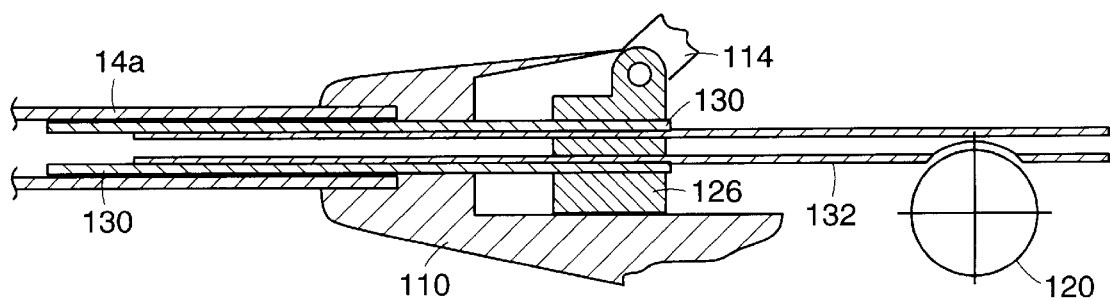
FIG. 4 is a cross sectional view of particular components of the device of FIG. 2.
Figure 6A:
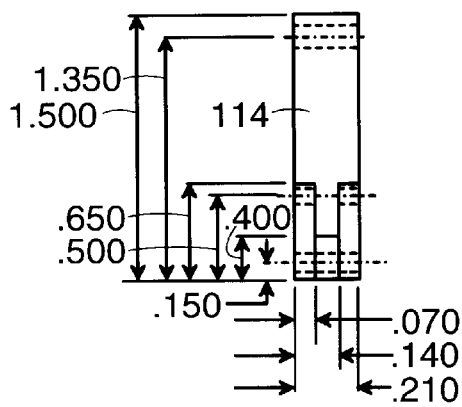
FIG. 6a is a rear view of a pivot arm shown in FIG. 2.
Figure 6B:
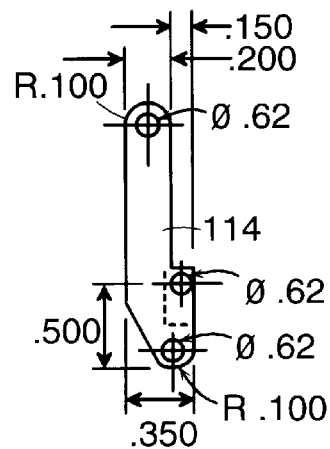
Figure 7A:
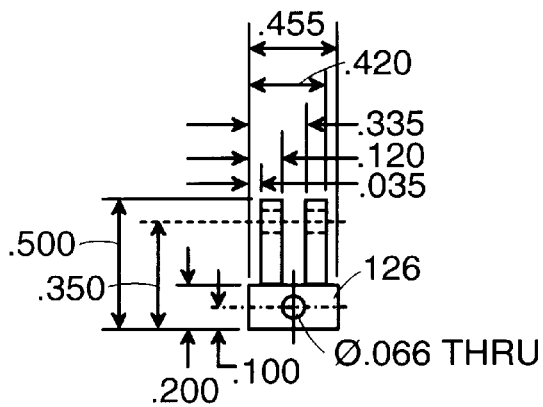
FIG. 7a is a front view of a coupler shown in FIG. 3.
Figure 7B:
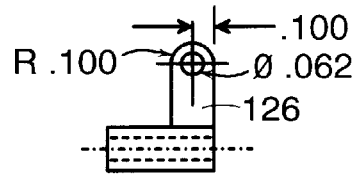
Figure 7C:
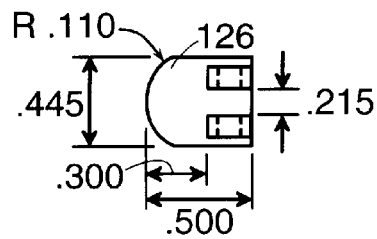
Figure 8A:
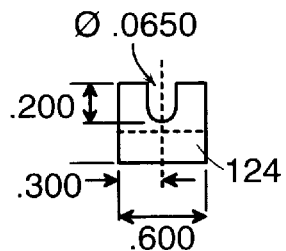
FIG. 8a is a side view of a roller mount shown in FIG. 3.
Figure 8B:
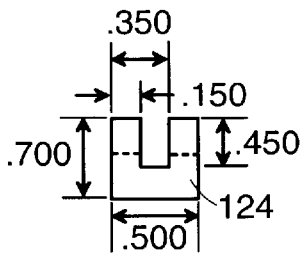
Figure 8C:
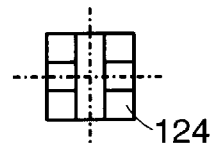
Figure 9A:
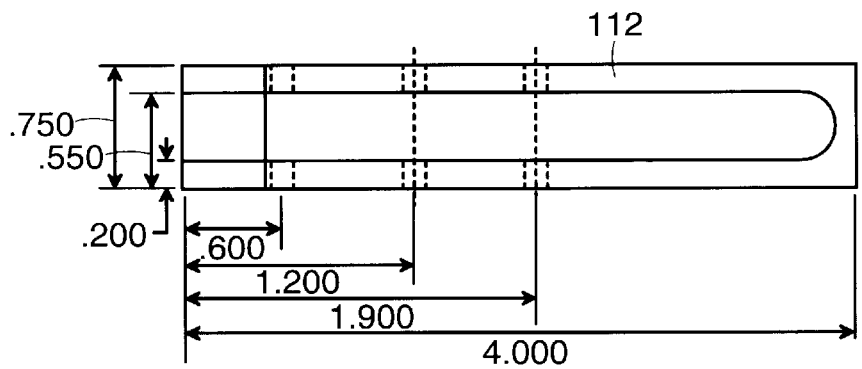
FIG. 9a is a bottom view of an advancing lever shown in FIG. 2.
Figure 9B:
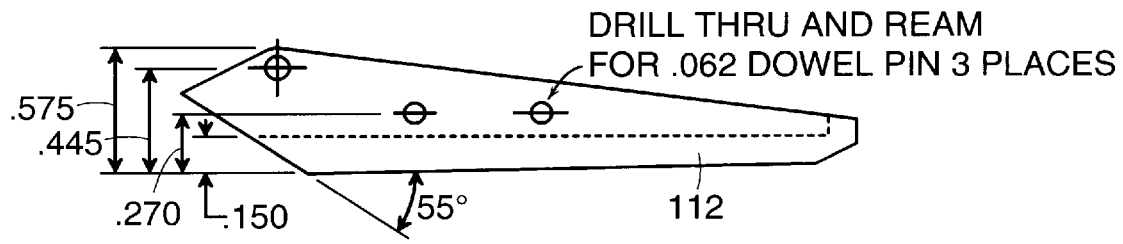
Figure 10A:
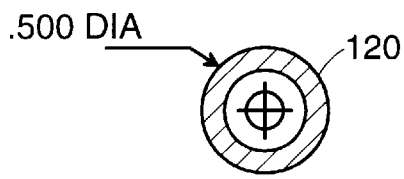
FIG. 10a is a cross sectional view of a drive roller shown in FIGS. 3 and 4.
Figure 10B:
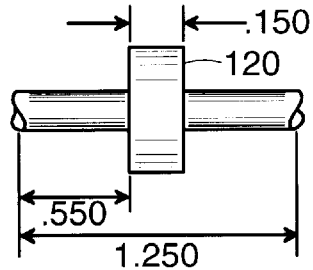

A hollow guide 132 shown in FIGS. 3 and 4 is connected to a proximal end portion of the housing 110 and extends into a proximal end of the tubular member 14a. The fiber F is capable of passing through the hollow guide 132. As shown in FIGS. 3, 4, 10a, and 10b, a rotatable driving roller 120 is provided for feeding the fiber F through the hollow guide 132. The driving roller 120 is rotatably mounted in a roller mount 124 shown in FIGS. 3, 8a, 8b, and 8c, and extends into the lumen of the hollow guide 132 via a slot in the hollow guide 132, as shown in FIG. 4.

Figure 2:
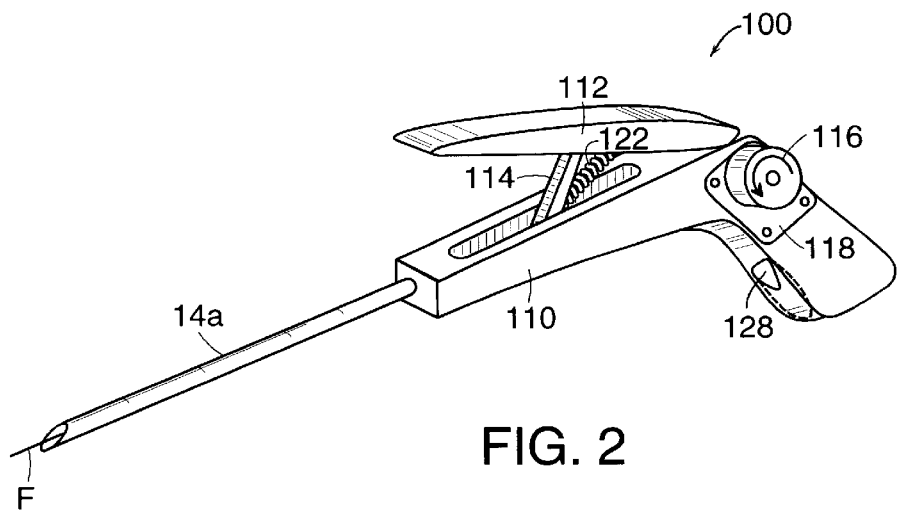
FIG. 2 is a perspective view of a second embodiment of the device.
Figure 11A:
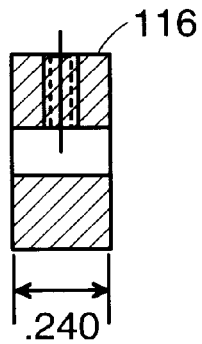
FIG. 11a is a cross sectional view of a driving knob shown in FIG. 2.
Figure 11B:
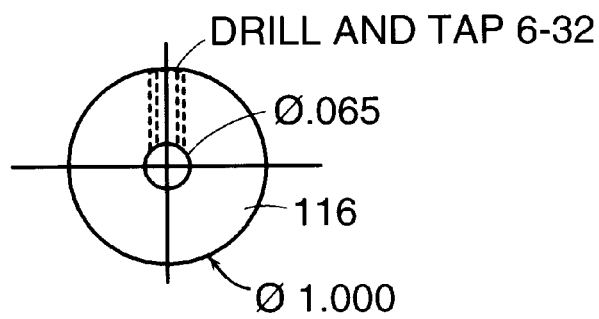
Figure 12A:
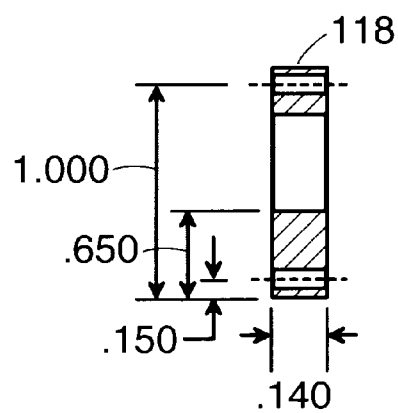
FIG. 12a is a cross sectional view of a drive mechanism cover shown in FIG. 2.
Figure 12B:
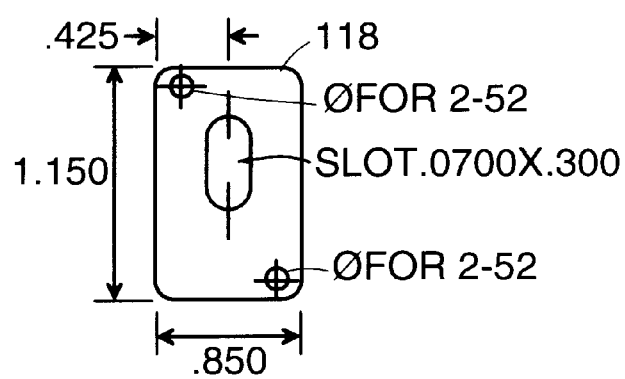

A driving knob 116, shown in FIGS. 2, 11a, and 11b, is coupled to the driving roller 120 so that rotation of the driving knob 116 rotates the driving roller 120. A drive mechanism cover 118 shown in FIGS. 2, 12a and 12b is mounted to the housing 110 to cover an opening in the housing 110 for accommodating the driving roller 120 and roller mount 124.

The device 100 also includes an adjustable tension screw 128 shown in FIGS. 2 and 3 for adjusting the distance between the outer surface of the driving roller 120 and an inner surface of the hollow guide 132. Adjustment of the tension screw 128 controls the degree of slippage between the outer surface of the driving roller 120 and the fiber F. This allows the device 110 to accommodate a number of different sizes of fiber F. Preferably, the outer surface of the driving roller 120 is designed to reduce slippage of the fiber F.

As shown in FIG. 3, an axially movable sleeve 130 is positioned between an outer surface of the hollow guide 132 and an inner surface of a proximal portion of the tubular member 14a, and between an outer surface of the hollow guide 132 and a distal portion of the housing 110. A coupler 126 shown in FIGS. 3, 4, 7a, 7b, and 7c is connected to a proximal end of the movable sleeve 126.

As shown in FIGS. 2, 3, 9a, and 9b, the device 100 also includes an advancing lever 112 having an end portion pivotally connected to the housing 110. A pivot arm 114 shown in FIGS. 2–4, 6a, and 6b has a first end pivotally connected to the advancing lever 112 and a second end pivotally connected to the coupler 126.

Pivoting of the advancing lever 112 with respect to the housing 110 transmits motion to the pivot arm 114 and coupler 126 to move the sleeve 130 about its axis. In other words, pivoting of the advancing lever 112 slides sleeve 130 distally or proximally in the tubular member 14a depending upon the direction of pivoting of the advancing lever 112. With reference to FIG. 3, counter clockwise pivoting of the advancing lever 112 with respect to the housing 110 moves the sleeve 130 distally, and clockwise pivoting of the advancing lever 112 moves the sleeve 130 proximally. Preferably, a spring 122 shown in FIGS. 2 and 3 has one end connected to the advancing lever 112 and another end connected to the pivot arm 114 to bias the advancing lever 112 in the clockwise direction after the lever 112 pivots in the counter clockwise direction.

To use the embodiment of FIGS. 2–4, the tubular member 14a is inserted into the body. The fiber material F is passed into an opening in a proximal end of the guiding member 132. The driving roller 116 is rotated to rotate the driving roller 120 and thereby feed fiber F through the guiding member 132 and into the lumen of the tubular member 14a. When the fiber F encounters body tissue at the opening of the distal portion of the tubular member 14a, the fiber F bunches up inside the distal portion of the tubular member 14a. After a sufficient amount of fiber F accumulates in the distal portion of the tubular member 14a, an operator pivots the advancing lever 112 counter clockwise toward the housing 110 to move the sleeve 130 in the distal direction. The distal end of the sleeve 130 moves against the bunched fiber in the tubular member 14a to force this fiber mass from the distal opening of the tubular member 14a and into a body.

When an operator releases the advancing lever 112, the spring 122 biases the lever 112 away from the housing 110 and thereby moves the sleeve 130 in the proximal direction to its original position. During movement of the sleeve 130 in the proximal direction, the outer surface of the driving roller 120 maintains contact with the fiber F to resist proximal movement of fiber F in the device 110.

Preferably, the inner diameter of the tubular member 14a is large enough to allow a sufficient amount of the fiber material to bunch together. In addition, a space for the fiber F could be created using a balloon or some mechanical device. The device 110 also preferably includes structure (not shown) for cutting the fiber F to separate the bunch of fiber from the rest of the fiber. The fiber F can be a suture or a thread.

FIGS. 13a, 13b, 13c, 14a, 14b, 14c, 14d, 15a, 15b, 16a, 16b, 16c, 17a, and 17b show a third embodiment of a device 200 for introducing fiber in the body. As shown in FIGS. 13a, 13b, 13c, 14a, 14b, 14c, and 14d, the device 200 includes a housing 210 having a passage extending along its length. A tubular member 14b shown in FIGS. 13a and 13b has a proximal end connected to a distal end of the housing 210. Preferably, the tubular member 14b is a tube or needle releasably coupled to the housing 210.

Figure 13A:
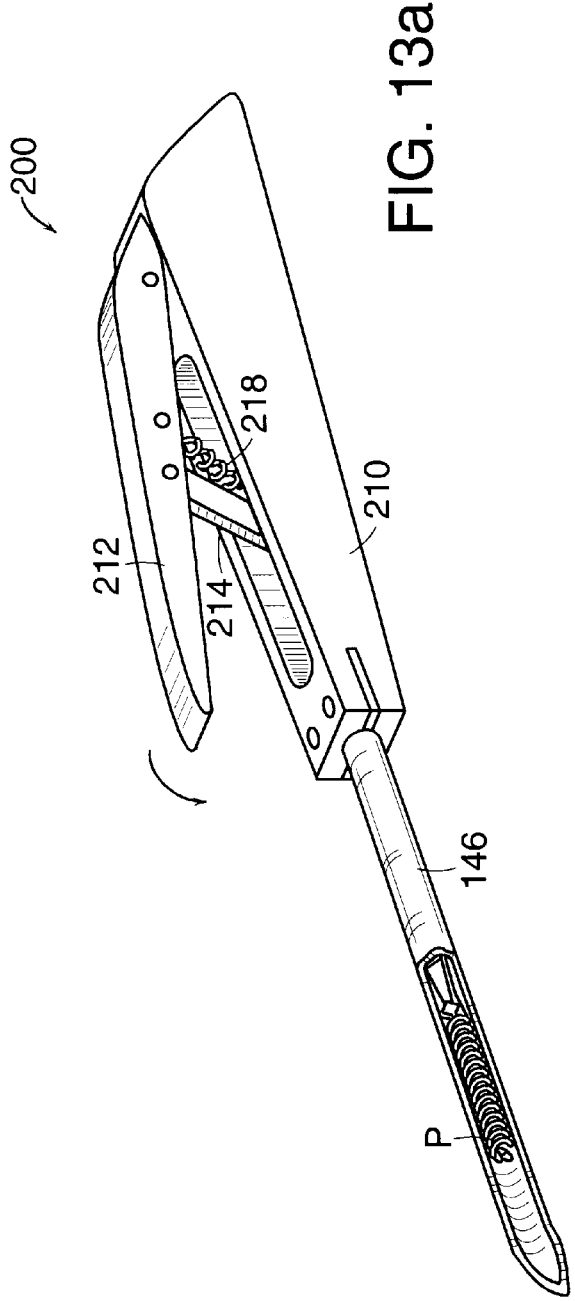
FIG. 13a is a perspective view of a third embodiment of the device.

As shown in FIG. 13a, an inner lumen of the tubular member 14b is preferably loaded with one or more pellets P of fiber, described below. Preferably, the tubular member 146 contains a plurality of pellets P, for example, ten.

Figure 13B:
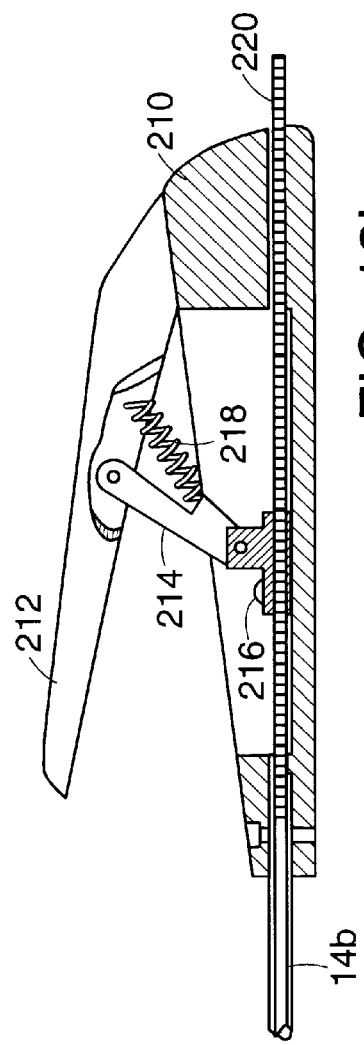
Figure 13C:
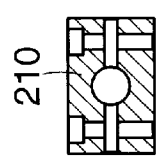
Figure 14D:
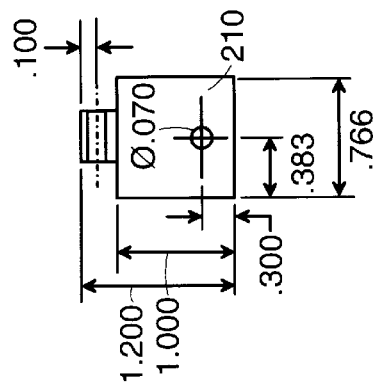
Figure 14A:
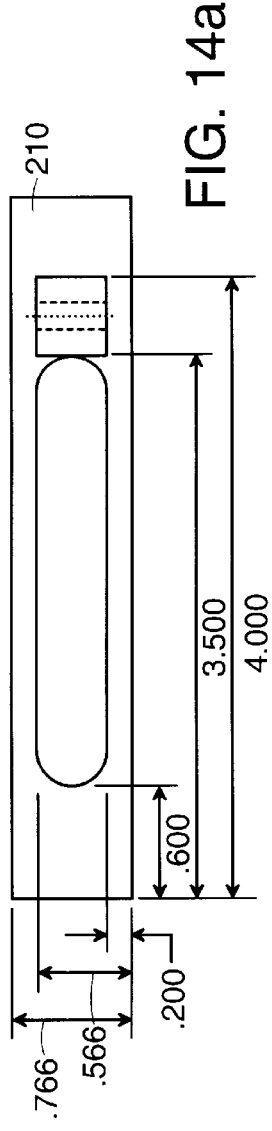
Figure 14B:
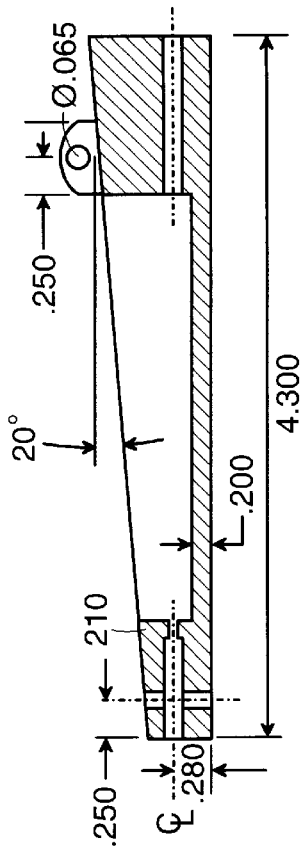
Figure 14C:
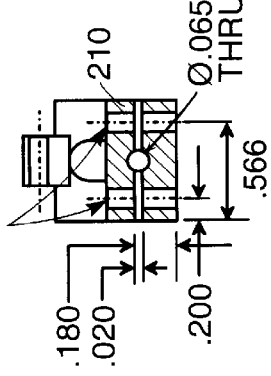
Figure 15A:
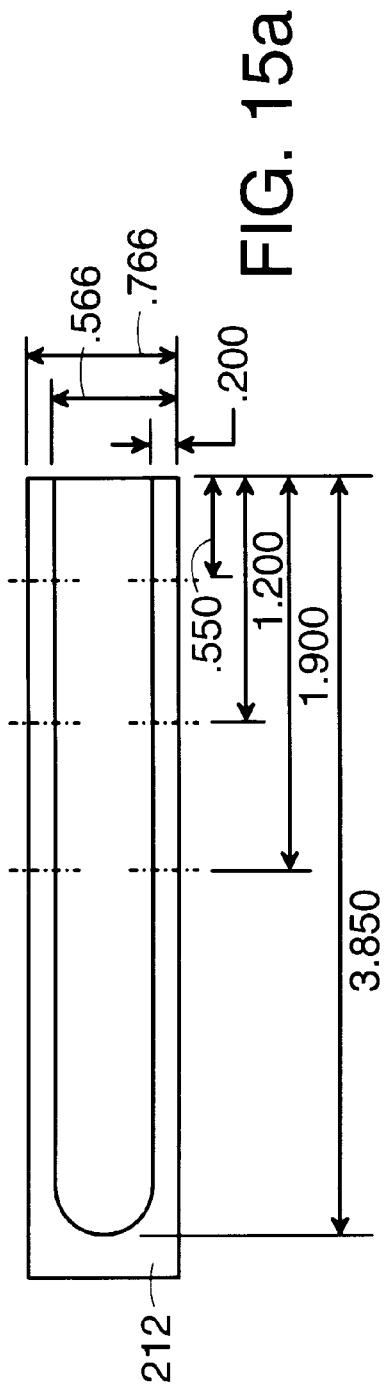
Figure 15B:
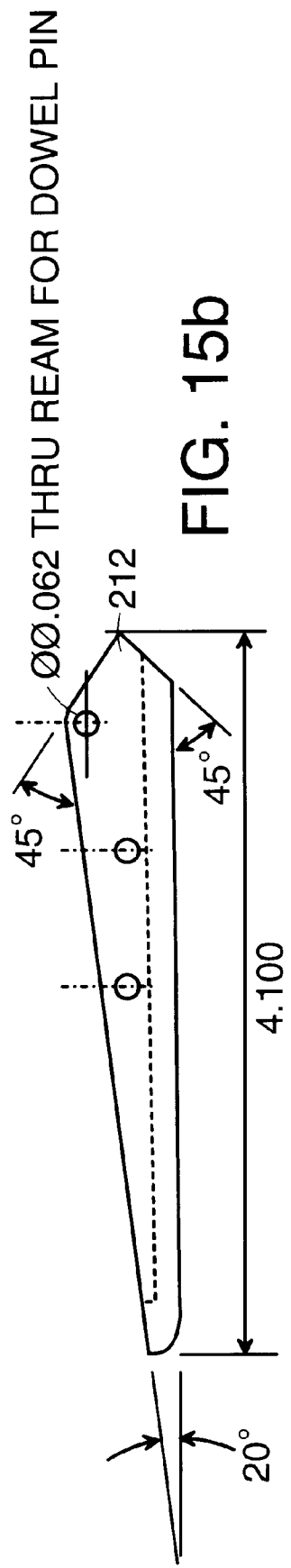
Figure 16A:
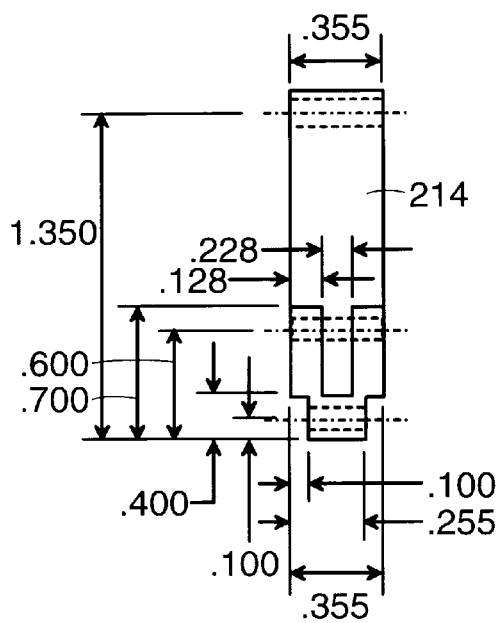
Figure 16B:
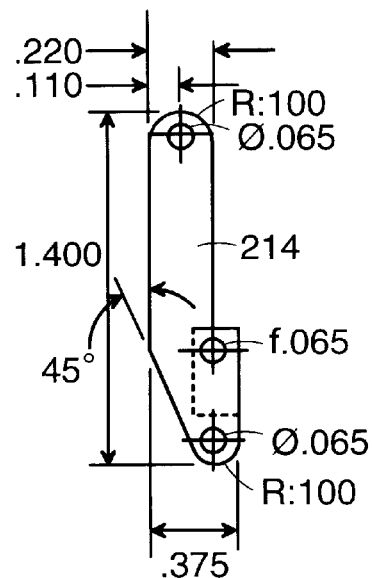
Figure 17A:
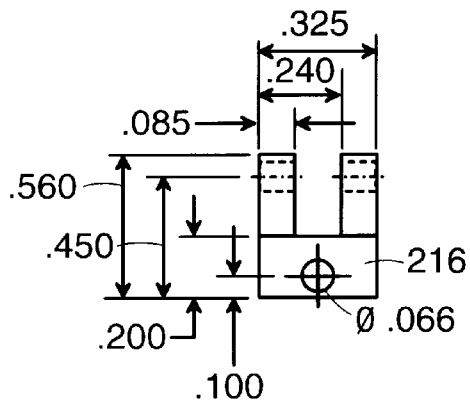
Figure 17B:
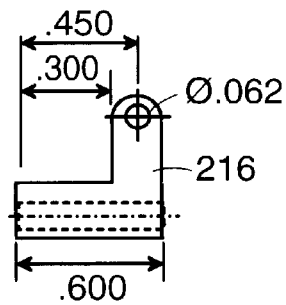
Figure 17C:
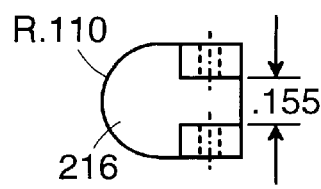

An axially movable push rod 220 shown in FIG. 13b extends in the longitudinal passage of the housing 210 and in the tubular member 14b. Similar to the embodiment of FIG. 2, the device 200 includes an advancing lever 212 (shown in FIGS. 13a, 13b, 15a, and 15b) pivotally connected to the housing 210, a coupler 216 (shown in FIGS. 17a, 17b, and 17c) connected to the push rod 220, a pivot arm 214 (shown in FIGS. 13a, 13b, 16a, and 16b) having one end pivotally connected to the advancing lever 212 and another end pivotally connected to the coupler 216, and a spring 218.

To use the device 200, the housing 210 is connected to the tubular member 14b loaded with one or more fiber pellets P and the tubular member 14b is inserted in the body. When the advancing lever 212 is pivoted toward the housing 210, the push rod 220 moves in the distal direction in the housing 210 and tubular member 14b. The distal end of the push rod 220 pushes one or more of the pellets P through an opening in a distal end of the tubular member 14b and into the body. Thereafter, the spring 218 returns the advancing lever 212 and push rod 220 to their original positions.

Optionally, the device 200 has unidirectional engagement mechanism (described below) and clutch mechanism (described below) for resisting proximal movement of the push rod when the advancing lever 212 returns to its original position. With such an arrangement, each depression of the advancing lever 212 moves the push rod 220 further in the distal direction so that more of the pellets P may be dispensed through the opening in the tubular member 14b.

FIG. 20 shows how the fiber pellet P is formed. A mandrel 310 is inserted into a pin vise 340 and an end portion of fiber F extending from a fiber spool 320 is secured to the pin vise 340. The pin vise 340 is rotated to wrap the fiber F helically around the mandrel 310. When a single layer of fiber F builds up on the mandrel 310, other layers are optionally wound on the initial layer. FIG. 18 shows an example of a fiber pellet P having 3 layers of helically wound fiber, and FIG. 19 shows an example of a fiber pellet P having 2 layers of helically wound fiber. For example, the pellet P is preferably about 1 inch to about 2 inches in length and made of nylon suture material.

After the fiber pellet P is formed, the pellet P is loaded in a tubular member of a device for introducing the pellet P. FIG. 21 shows one example of how the pellet P is loaded in a tubular member 14c, such as a tube or needle. The pellet P is inserted in a lumen of the tubular member 14c and the mandrel 310 is removed from the pellet P. Optionally, additional pellets P are inserted in the tubular member 14c in the same manner.

FIG. 22 shows another example of how a pellet P is loaded in a tubular member 14d, such as a tube or needle. Initially, one or more pellets P are loaded in a cartridge 440 in the same way that the pellet P is inserted in the tubular member 14c shown in FIG. 21. Then the cartridge 440 is coupled to an adapter 410 on the proximal end of the tubular member 14d. A pushing member 450 is then used to push the pellet(s) P from the cartridge 440 into the tubular member 14d.

Figure 23:
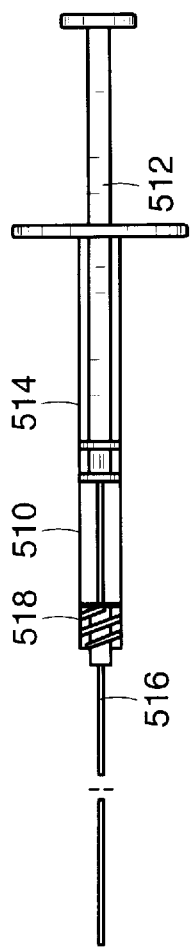
FIG. 23 is a view of a push rod advancing apparatus for use with a fourth embodiment of the invention.

FIGS. 23–27 show another device for delivering fiber into a body. As shown in FIG. 23, this embodiment includes a syringe 510 having a plunger 512 slidable in a barrel 514. A threaded luer adapter 518 is provided at the distal end of the barrel 514. A push rod 516 extends from a distal end of the plunger 512 and through a distal opening in the barrel 514. Movement of the plunger 512 in the barrel 514 moves the push rod 516 axially.

Figure 24:
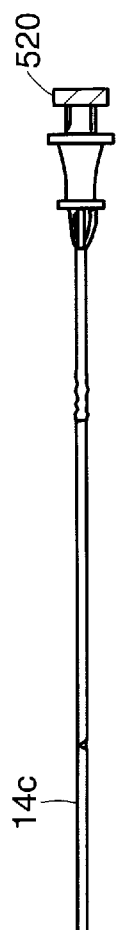
FIG. 24 is a side view of a needle for mounting to the device of FIG. 23.
Figure 25:
FIG. 25 is a view of tubular cartridge loaded with a fiber pellet.
Figure 26:
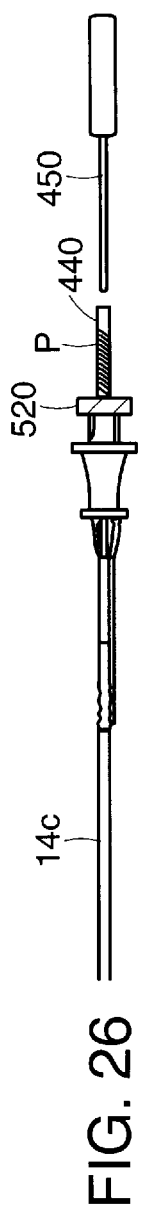
FIG. 26 is a view showing how the fiber pellet in the cartridge of FIG. 25 is loaded in the needle of FIG. 24.
Figure 27:
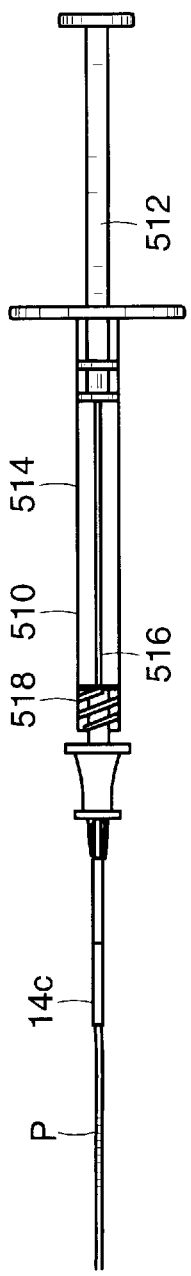
FIG. 27 is a view showing the needle of FIG. 24 mounted to the advancing apparatus of FIG. 23 to deliver the fiber pellet.

A tubular member 14e shown in FIGS. 24, 26, and 27 has a threaded luer adapter 520 capable of being connected to the luer adapter 518 on the syringe barrel 514, as shown in FIG. 27. Preferably, tubular member 14e is a tube or needle, and the luer adapter 520 on the tubular member 14e is capable of being connected to a cystoscope for use in imaging the urethra.

As shown in FIG. 27, the tubular member 14e is preferably loaded with one or more of the fiber pellets P. The tubular member 14e is preferably loaded with the fiber pellet(s) P in the same way in which the tubular member 14d shown in FIG. 22 is loaded with pellet(s) P. In other words, one or more of the pellets P are pushed into the tubular member 14e from a cartridge 440 shown in FIGS. 25 and 26 by a pushing member 450.

After one or more pellets P are loaded in the tubular member 14e and the tubular member 14e is connected to the barrel 514, the tubular member 14e is inserted in the body. An operator moves the plunger 512 in the distal direction to extend the push rod 516 in the tubular member 14e. The distal end of the push rod 516 pushes one or more of the pellets P from a distal end of the tubular member 14e and into the body via an opening in the tubular member 14e.

If more pellets P need to be loaded into the tubular member 14e during a procedure, the syringe barrel 514 is removed from the tubular member 14e, optionally while the tubular member 14e is still inserted in the body. Thereafter, the pellets P are loaded with the structure shown in FIG. 26.

For example, the distance from the distal end of the tubular member 14e needle to its connector 520 is 14 inches, and the length of the push rod 516 is 15 inches.

Figure 28:
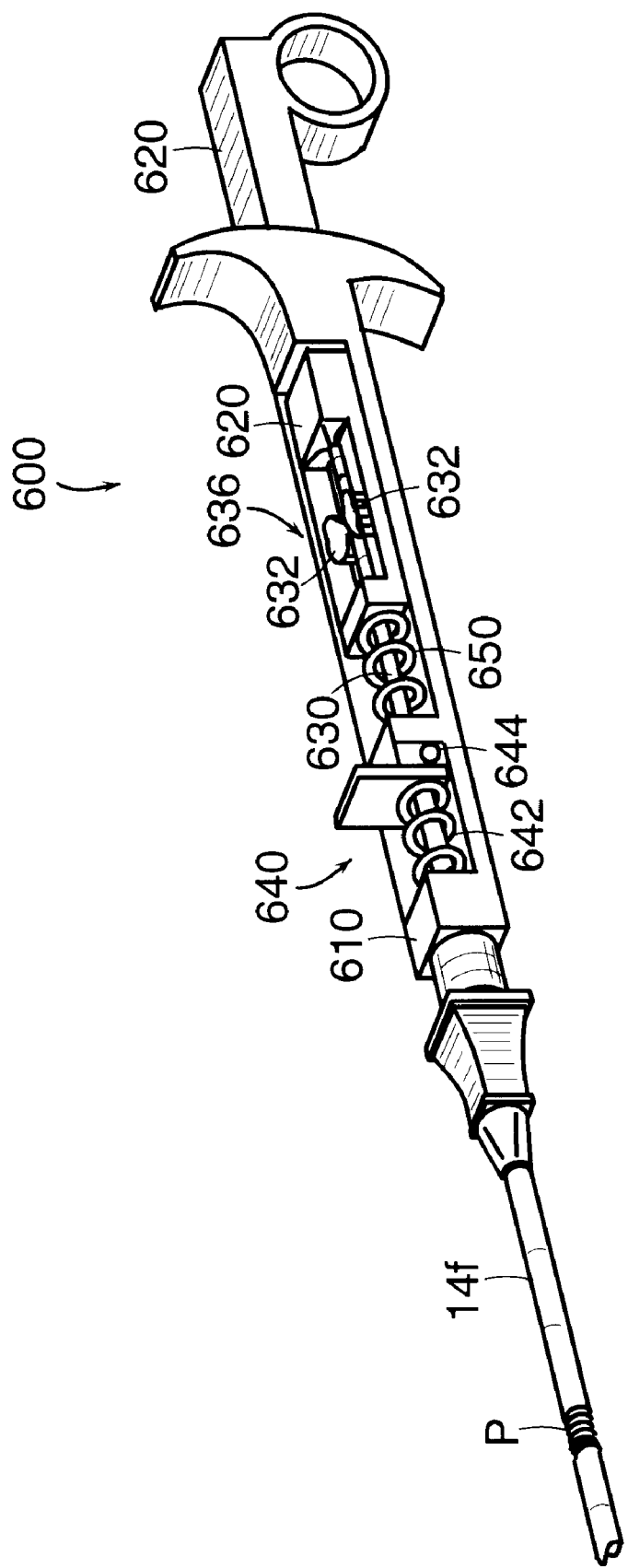
FIG. 28 is a perspective view of a fifth embodiment of the device.

FIG. 28 shows another device 600 for introducing fiber into the body. The device 600 includes a housing 610 and a tubular member 14f connected to the housing 601). Preferably, the tubular member 14f is a needle or tube releasably connected of the housing 610. In addition, the tubular member 14f is preferably loaded with a plurality of the pellets P.

A slide 620 is movable in a proximal end portion of the housing 610. A push rod 630 extends through a passage in the slide 620 and into the tubular member 14f. The slide 620 has a unidirectional engagement mechanism 636 including a pair of pivoting cams 632. The unidirectional engagement mechanism 636 engages an outer surface of the push rod 630 when the slide 620 is moved in the distal direction, and disengages from the push rod 630 when the slide 620 moves in the proximal direction. In other words, the mechanism 636 may function in a manner similar to a cleat used on a sail boat.

The device 600 also includes a return spring 650 and one-way clutch mechanism 640 having a clutch spring 642 and clutch pad 644. The return spring 650 forces the slide 620 in the proximal direction after the slide 620 moves in the distal direction. The one-way clutch mechanism 640 allows distal movement of the push rod 630 and resists proximal movement of the push rod 630. Movement of the slide 620 in the distal direction overcomes a biasing force of the clutch spring 642 and moves the clutch pad 644 out of engagement with the push rod 630. Proximal movement of the slide 620 allows the clutch spring 642 to place the clutch pad 644 into engagement with the push rod 630.

To use the device 600, fiber pellets P are loaded in the tubular member 14f and the tubular member 14f is connected to the housing 610. The tubular member 14f is inserted in the body and the slide 620 is moved in the distal direction with respect to the housing 610. The unidirectional engagement mechanism 636 engages an outer surface of the push rod 630 and the one-way clutch mechanism 640 is placed out of engagement with the push rod 630. This allows the push rod 630 to move in the distal direction along with the slide 620. The distal end of the push rod 630 pushes one or more fiber pellets P through the opening in the tubular member 14f.

When the slide 620 is released, the return spring 650 moves the slide 620 proximally back to its original position. The unidirectional engagement mechanism 636 releases its engagement with an outer surface of the push rod 630 and the one-way clutch mechanism 640 engages with the push rod 630. This resists movement of the push rod 630 in the proximal direction.

Repeated distal movement and release of the slide 620 advances the push rod 630 further toward the distal end of tubular member 14f and thereby allows for continued dispensing of fiber pellets P from the tubular member 14f without the need to reload the device 600.

Preferably, each of the devices mentioned above is used to dispense fiber or fiber pellets for bulking tissue. For example, these devices are preferably used to provide tissue bulking for treating incontinence.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A device for introducing fiber material into a body, comprising:

a tubular member having a lumen extending to an axial opening in a distal end portion of the tubular member; and a helical member rotatable within the tubular member to convey the fiber material through at least one portion of the lumen, out of the opening and into the body.

2. The device of claim 1 further comprising a syringe coupled to the tubular member for delivering the fiber material into the lumen of the tubular member.

3. The device of claim 2 further comprising the fiber material.

4. A device for introducing a fiber material into a body, comprising:

a tubular member having a lumen extending to an opening in a distal end portion of the tubular member;

a sleeve slidable within the tubular member to force the fiber material through at least a portion of the lumen, out of the opening, and into the body; and a lever having a proximal end and a distal end, wherein the distal end is rotatably connected to said slidable sleeve and wherein radial motion of the proximal end of the lever imparts longitudinal motion to the distal end of the lever and the slidable sleeve.

5. The device of claim 4 further comprising a driving roller for feeding the fiber material into a distal portion of the tubular member until the fiber material accumulates inside the distal portion such that the sleeve can be moved to force the accumulated fiber material out of the opening in the distal end portion of the tubular member and into the body.

6. The device of claim 5 further comprising the fiber material.

7. A device for introducing a fiber material into a body, comprising:

a tubular member having a lumen extending to an opening in a distal end portion of the tubular member;

a slide;

a push rod slidable within the tubular member to push the fiber material through at least a portion of the lumen, out of the opening, and into the body; and a pair of pivoting cams engaging the rod when the slide is moved distally and disengaging from the rod when the slide is moved proximally.

8. The device of claim 7 further comprising the fiber material.

9. A method for introducing fiber material into a body, comprising:

providing a device including (i) a tubular member having a lumen extending to an axial opening in a distal end portion of the tubular member and (ii) a helical member rotatable within the tubular member for passing the fiber material through the lumen and the opening and into the body;

introducing the tubular member into the body; and rotating the helical member within the tubular member to pass the fiber material through the opening in the distal end portion of the tubular member into the body.

10. A method for introducing fiber material into a body, comprising:

providing a device including (i) a tubular member having a lumen extending to an opening in a distal end portion of the tubular member, (ii) a sleeve slidable within the tubular member for passing the fiber material through the lumen and the opening and into the body; and (iii) a lever having a proximal end and a distal end, wherein the distal end is rotatably connected to said slidable sleeve and wherein radial motion of the proximal end of the lever imparts longitudinal motion to the distal end of the lever and the slidable sleeve;

introducing the tubular member into the body; and moving the proximal end of the lever radially to slide the sleeve within the tubular member and pass the fiber material through the opening in the distal end portion of the tubular member into the body.

11. A method for introducing fiber material into a body, comprising:

providing a device including (i) a tubular member having a lumen extending to an opening in a distal end portion of the tubular member, (ii) a slide, (iii) a push rod slidable within the tubular member to push the fiber material through at least a portion of the lumen, out of the opening and into the body, and (iv) a pair of pivoting cams engaging the rod when the slide is moved distally and disengaging from the rod when the slide is moved proximally;

introducing the tubular member into the body; and sliding the slide to engage the cams onto the push rod and push the push rod thereby passing the fiber material through the opening in the distal end portion of the tubular member.

12. The device of any of claims 1, 4, or 7, wherein the device further comprises a cutting mechanism to cut the fiber material as it is passes through the opening in the distal end portion of the tubular member into the body.

13. The method of any of claims 9, 10, or 11, further comprising the step of cutting the fiber material as it passes through the opening in the distal end portion of the tubular member into the body.

14. The device of claim 3 wherein the fiber material further comprise, particles in a carrier.

15. The device of claim 6 wherein the fiber material further comprises a suture.

16. The device of claim 8 wherein the fiber material further comprises one or more pellets.

* * * * *